(12) United States Patent
Yeh et al.

(10) Patent No.: US 12,714,843 B2
(45) Date of Patent: Aug. 25, 2026

(54) NEEDLESS CONNECTOR WITH SUPPORT MEMBER

(71) Applicant: CareFusion 303, Inc., San Diego, CA (US)

(72) Inventors: Jonathan Yeh, Brea, CA (US); Christopher J. Zollinger, Chino Hills, CA (US); George Michel Mansour, Diamond Bar, CA (US); Matthew Quach, San Gabriel, CA (US)

(73) Assignee: CAREFUSION 303, INC.

( * ) Notice: Subject to any disclaimer, the term of this patent is extended or adjusted under 35 U.S.C. 154(b) by 0 days.

(21) Appl. No.: 18/348,833

(22) Filed: Jul. 7, 2023

(65) Prior Publication Data

US 2023/0347131 A1 Nov. 2, 2023

Related U.S. Application Data

(63) Continuation of application No. 17/323,835, filed on May 18, 2021, now Pat. No. 11,730,944, which is a (Continued)

(51) Int. Cl.

| | |
|---|---|
| ***A61M 39/24*** | (2006.01) |
| ***A61M 39/10*** | (2006.01) |
| ***A61M 39/26*** | (2006.01) |

(52) U.S. Cl.

CPC ............ *A61M 39/24* (2013.01); *A61M 39/10* (2013.01); *A61M 39/26* (2013.01); *A61M 2039/2406* (2013.01); *A61M 2039/2433* (2013.01)

(58) Field of Classification Search

CPC ....... A61M 39/20; A61M 39/24; A61M 39/26

See application file for complete search history.

(56) References Cited

U.S. PATENT DOCUMENTS

| | | | |
|---|---|---|---|
| 3,192,949 | A | 7/1965 | De See |
| 4,141,379 | A | 2/1979 | Manske |

(Continued)

FOREIGN PATENT DOCUMENTS

| | | | |
|---|---|---|---|
| AU | 2010320036 | A1 | 5/2012 |
| CN | 1077654 | | 10/1993 |

(Continued)

OTHER PUBLICATIONS

Japanese Office Action for Application No. 2024-009189, dated Sep. 4, 2024, 4 pages including translation.

(Continued)

*Primary Examiner* — Scott J Medway

(74) *Attorney, Agent, or Firm* — MASCHOFF BRENNAN

(57) ABSTRACT

Needleless connectors are described herein. A needleless connector includes a body, a valve element at least partially disposed within the body, and a base. The valve element includes a cylindrical portion having an outwardly extending flange at a distal end. The flange has a bottom surface with an outer area and an inner area. The base includes a rim having a top surface that is in contact with an outer area of the flange of the valve element, the rim defining a recess with a bottom surface separated from the top surface of the rim, and at least one support member having a top surface spaced apart from the top surface of the rim and configured to resist deformation of the flange toward the recess.

16 Claims, 7 Drawing Sheets

Related U.S. Application Data continuation of application No. 14/745,199, filed on Jun. 19, 2015, now Pat. No. 11,033,726, which is a continuation of application No. 13/829,187, filed on Mar. 14, 2013, now Pat. No. 9,089,682.

(56) References Cited

U.S. PATENT DOCUMENTS

| | | | |
|---|---|---|---|
| 4,535,820 A | 8/1985 | Raines | |
| 4,654,031 A | 3/1987 | Lentz | |
| 4,712,583 A | 12/1987 | Pelmulder et al. | |
| 4,911,403 A | 3/1990 | Lockwood, Jr. | |
| 5,061,253 A * | 10/1991 | Yoshida | A61M 39/26 604/246 |
| 5,085,645 A * | 2/1992 | Purdy | A61M 39/26 604/167.03 |
| 5,092,857 A | 3/1992 | Fleischhacker | |
| 5,242,432 A | 9/1993 | DeFrank | |
| 5,289,849 A | 3/1994 | Paradis | |
| 5,401,255 A | 3/1995 | Sutherland et al. | |
| 5,439,451 A | 8/1995 | Collinson et al. | |
| 5,501,426 A | 3/1996 | Atkinson et al. | |
| 5,549,651 A | 8/1996 | Lynn | |
| 5,555,908 A | 9/1996 | Edwards et al. | |
| 5,569,235 A | 10/1996 | Ross | |
| 5,613,663 A | 3/1997 | Schmidt et al. | |
| 5,623,969 A | 4/1997 | Raines | |
| 5,676,346 A | 10/1997 | Leinsing | |
| 5,690,612 A | 11/1997 | Lopez et al. | |
| 5,699,821 A | 12/1997 | Paradis | |
| 5,730,418 A | 3/1998 | Feith et al. | |
| 5,782,816 A | 7/1998 | Werschmidt et al. | |
| 5,806,551 A | 9/1998 | Meloul et al. | |
| 5,992,462 A | 11/1999 | Atkinson et al. | |
| 5,996,631 A | 12/1999 | Thronton | |
| 6,024,729 A | 2/2000 | Dehdashtian et al. | |
| 6,050,978 A | 4/2000 | Orr et al. | |
| 6,245,048 B1 | 6/2001 | Fangrow, Jr. et al. | |
| 6,261,282 B1 | 7/2001 | Jepson | |
| 6,651,956 B2 | 11/2003 | Miller | |
| 6,679,219 B1 | 1/2004 | Pacinelli | |
| 6,883,778 B1 | 4/2005 | Newton et al. | |
| 6,886,803 B2 | 5/2005 | Mikiya et al. | |
| 7,184,825 B2 | 2/2007 | Leinsing et al. | |
| 7,360,556 B2 | 4/2008 | Mijers | |
| 7,497,848 B2 | 3/2009 | Leinsing | |
| 7,559,530 B2 | 7/2009 | Korogi et al. | |
| 7,600,530 B2 | 10/2009 | Truitt | |
| 7,789,864 B2 | 9/2010 | Cote, Sr. et al. | |
| 7,887,519 B2 | 2/2011 | Cote, Sr. et al. | |
| 7,971,804 B2 | 7/2011 | Roberts | |
| 8,062,261 B2 | 11/2011 | Adams | |
| 8,291,936 B2 | 10/2012 | Carmody et al. | |
| 8,298,196 B1 | 10/2012 | Mansour | |
| 8,511,638 B2 * | 8/2013 | Mansour | A61M 39/26 251/149.6 |
| 8,568,371 B2 | 10/2013 | Siopes et al. | |
| 8,720,065 B2 | 5/2014 | Christensen et al. | |
| 9,089,682 B2 | 7/2015 | Yeh et al. | |
| 9,138,572 B2 | 9/2015 | Zeytoonian et al. | |
| 9,278,205 B2 | 3/2016 | Quach | |
| 2002/0002351 A1 | 1/2002 | Cote, Sr. | |
| 2002/0133124 A1 | 9/2002 | Leinsing et al. | |
| 2002/0193752 A1 | 12/2002 | Lynn | |
| 2003/0050610 A1 | 3/2003 | Newton et al. | |
| 2003/0098430 A1 | 5/2003 | Leinsing et al. | |
| 2004/0124389 A1 | 7/2004 | Phillips | |
| 2004/0195538 A1 | 10/2004 | Raines et al. | |
| 2004/0227120 A1 | 11/2004 | Raybuck | |
| 2005/0059952 A1 | 3/2005 | Giuliano et al. | |
| 2005/0222541 A1 | 10/2005 | Lopez et al. | |
| 2006/0025724 A1 | 2/2006 | Chen | |
| 2006/0027270 A1 | 2/2006 | Truitt et al. | |
| 2006/0089603 A1 | 4/2006 | Truitt et al. | |
| 2006/0108555 A1 | 5/2006 | Kiehne | |
| 2006/0163515 A1 | 7/2006 | Ruschke | |
| 2006/0208210 A1 | 9/2006 | Raybuck | |
| 2007/0083162 A1 | 4/2007 | O'Reagan et al. | |
| 2007/0100295 A1 | 5/2007 | Belley et al. | |
| 2007/0191786 A1 | 8/2007 | Raines et al. | |
| 2007/0218757 A1 | 9/2007 | Guala | |
| 2007/0270756 A1 | 11/2007 | Peppel et al. | |
| 2008/0087859 A1 | 4/2008 | Enerson | |
| 2008/0108956 A1 | 5/2008 | Lynn et al. | |
| 2008/0169444 A1 | 7/2008 | Guala | |
| 2009/0030401 A1 | 1/2009 | Phillips | |
| 2009/0057589 A1 | 3/2009 | Thorne, Jr. et al. | |
| 2009/0184275 A1 | 7/2009 | Ruschke et al. | |
| 2009/0299300 A1 | 12/2009 | Truitt | |
| 2010/0036330 A1 | 2/2010 | Plishka et al. | |
| 2010/0063482 A1 | 3/2010 | Mansour et al. | |
| 2010/0076381 A1 | 3/2010 | Simonsen | |
| 2010/0234798 A1 | 9/2010 | Huang | |
| 2010/0256573 A1 | 10/2010 | Mansour et al. | |
| 2011/0024664 A1 | 2/2011 | Burnard et al. | |
| 2011/0028914 A1 | 2/2011 | Mansour et al. | |
| 2011/0028915 A1 | 2/2011 | Siopes | |
| 2011/0046573 A1 | 2/2011 | Newton et al. | |
| 2011/0130724 A1 | 6/2011 | Mansour et al. | |
| 2011/0152787 A1 | 6/2011 | Truitt et al. | |
| 2011/0282302 A1 | 11/2011 | Lopez | |
| 2011/0319859 A1 | 12/2011 | Zeytoonian et al. | |
| 2012/0310179 A1 | 12/2012 | Truitt et al. | |
| 2012/0316514 A1 | 12/2012 | Mansour | |
| 2013/0030386 A1 | 1/2013 | Panian et al. | |
| 2013/0190684 A1 | 7/2013 | Panian et al. | |
| 2013/0193359 A1 | 8/2013 | Yeh | |

FOREIGN PATENT DOCUMENTS

| | | |
|---|---|---|
| CN | 1139010 | 1/1997 |
| CN | 1305391 | 7/2001 |
| CN | 1802183 A | 7/2006 |
| CN | 101035591 A | 9/2007 |
| CN | 101224320 A | 7/2008 |
| CN | 101879339 A | 11/2010 |
| CN | 102448537 A | 5/2012 |
| CN | 102481445 | 5/2012 |
| CN | 102497897 | 6/2012 |
| CN | 202282846 U | 6/2012 |
| CN | 102686265 | 9/2012 |
| CN | 102686266 A | 9/2012 |
| CN | 202751639 U | 2/2013 |
| EP | 2075032 | 7/2009 |
| EP | 2411085 | 2/2012 |
| EP | 2719419 | 4/2014 |
| JP | H0857058 | 3/1996 |
| JP | H09182790 | 7/1997 |
| JP | 2002514475 | 5/2002 |
| JP | 2005511162 | 4/2005 |
| JP | 2005261931 A | 9/2005 |
| JP | 2007500537 | 1/2007 |
| JP | 2008517653 | 5/2008 |
| JP | 2008522729 | 7/2008 |
| JP | 2008264030 | 11/2008 |
| JP | 2009148561 | 7/2009 |
| JP | 2011036691 A | 2/2011 |
| JP | 366779 | 3/2011 |
| JP | 2011147809 | 8/2011 |
| JP | 20125605 | 1/2012 |
| JP | 2012501743 A | 1/2012 |
| JP | 201224565 | 2/2012 |
| JP | 2012530555 A | 12/2012 |
| JP | 2013500128 | 1/2013 |
| JP | 2013022415 | 2/2013 |
| JP | 2016514014 A | 5/2016 |
| WO | WO-9826835 | 6/1998 |
| WO | WO-2004082756 | 9/2004 |
| WO | WO-2004112866 | 12/2004 |
| WO | WO-2005011799 | 2/2005 |
| WO | WO-2006047181 A2 | 5/2006 |
| WO | WO-2006078355 | 7/2006 |
| WO | WO-2006124981 A1 | 11/2006 |
| WO | WO-2008091698 | 7/2008 |

(56) References Cited

FOREIGN PATENT DOCUMENTS

| | | |
|---|---|---|
| WO | WO-2010151507 | 12/2010 |
| WO | WO-2011014265 | 2/2011 |
| WO | WO-2011060384 | 5/2011 |
| WO | WO-2011119347 | 9/2011 |
| WO | WO-2013016077 | 1/2013 |
| WO | WO-2013099261 | 7/2013 |
| WO | WO-2013122148 | 8/2013 |
| WO | WO-2014143530 A1 | 9/2014 |

OTHER PUBLICATIONS

European Extended Search Report for Application No. 23158100.0, dated Jan. 4, 2024, 10 pages.
European Office Action for Application No. 21167645.7, dated Apr. 23, 2024, 5 pages.
Extended European Search Report for Application No. 24167354.0, dated Jul. 3, 2024, 7 pages.
Australian Examination Report No. 1 for Application No. 2014228543, dated Sep. 26, 2017, 2 pages.
Australian Examination Report No. 1 for Application No. 2014228618, dated Aug. 30, 2017, 3 pages.
Australian Examination Report No. 1 for Application No. 2014228626, dated Aug. 4, 2017, 3 pages.
Australian Examination Report No. 1 for Application No. 2014242176, dated Sep. 5, 2017, 2 pages.
Australian Examination Report No. 1 for Application No. 2014248948, dated Feb. 28, 2018, 4 pages.
Australian Examination Report No. 2 for Application No. 2014242176, dated Apr. 16, 2018, 3 pages.
Australian Examination Report No. 2 for Application No. 2014248948, dated Jul. 16, 2018, 4 pages.
Australian Office Action for Application No. 2018214010, dated Aug. 1, 2019, 2 pages.
Australian Office Action for Application No. 2018278973, Aug. 9, 2019, 4 pages.
Australian Office Action for Application No. 2019201757, dated Aug. 1, 2019, 2 pages.
Australian Office Action for Application No. 2019279901, dated Dec. 3, 2020, 4 pages.
Australian Office Action for Application No. 2020202010, dated Dec. 11, 2020, 3 pages.
Australian Office Action for Application No. 2020210179, dated Jul. 20, 2021, 2 pages.
Australian Office Action for Application No. 2021203375, dated May 20, 2022, 3 pages.
Australian Office Action for Application No. 2021269422, Aug. 23, 2023, 6 pages.
Australian Office Action for Application No. 2021269422, dated Mar. 6, 2023, 4 pages.
Australian Examination Report No. 1 for Application No. 2014228627, dated Mar. 14, 2018, 3 pages.
Canadian Office Action for Application No. 2901177, dated Dec. 6, 2019, 3 pages.
Canadian Office Action for Application No. 2901180, dated Dec. 9, 2019, 3 pages.
Canadian Office Action for Application No. 2901592, dated Dec. 17, 2019, 6 pages.
Canadian Office Action for Application No. 2901592, dated Jul. 21, 2020, 4 pages.
Canadian Office Action for Application No. 2901673, dated Dec. 11, 2019, 3 pages.
Canadian Office Action for Application No. 2901772, dated Dec. 16, 2019, 3 pages.
Canadian Office Action for Application No. 2904891, dated Apr. 2, 2020, 7 pages.
Canadian Office Action for Application No. 3118642, dated Aug. 26, 2022, 5 pages.
Chinese Office Action for Application No. 201480014352.0, dated Feb. 2, 2018, 5 pages excluding English translation.
Chinese Office Action for Application No. 201480014352.0, dated Mar. 15, 2019, 7 pages.
Chinese Office Action for Application No. 201480014352.0, dated Oct. 22, 2019, 17 pages.
Chinese Office Action for Application No. 2014800143520, dated Dec. 5, 2016, 7 pages.
Chinese Office Action for Application No. 201480014557.9, dated Apr. 10, 2018, 8 pages.
Chinese Office Action for Application No. 201480014557.9, dated Jan. 23, 2019, 11 pages.
Chinese Office Action for Application No. 201480014557.9, dated Jul. 9, 2020, 22 pages.
Chinese Office Action for Application No. 201480014557.9, dated Mar. 11, 2020, 13 pages.
Chinese Office Action for Application No. 201480014557.9, dated Mar. 3, 2017, 6 pages excluding English translation.
Chinese Office Action for Application No. 201480014965.4, dated Mar. 3, 2017, 9 pages excluding English translation.
Chinese Office Action for Application No. 201480014971.X, dated Feb. 21, 2017, 6 pages excluding English translation.
Chinese Office Action for Application No. 201480015027.6, dated Mar. 10, 2017, 7 pages excluding English translation.
Chinese Office Action for Application No. 201480015065.1, dated Feb. 22, 2017, 7 pages excluding English translation.
Chinese Office Action for Application No. 201810058864.7, dated Mar. 27, 2020, 11 pages.
Chinese Office Action for Application No. 201810082331.2, dated Apr. 2, 2020, 12 pages.
Chinese Office Action for Application No. 201810082331.2, dated Nov. 17, 2020, 6 pages.
Chinese Office Action for Application No. 201910444553.9, dated Mar. 21, 2022, 8 pages including translation.
Chinese Office Action for Application No. 201910444553.9, dated Sep. 18, 2021, 9 pages including translation.
Chinese Patent Application No. 201910444553.9, dated Jan. 6, 2021, 8 pages including translation.
Chinese Second Office Action for 201480014352.0, dated Jun. 21, 2017, 7 pages excluding translation.
Chinese Second Office Action for Application No. 201480014557.9, dated Oct. 23, 2017, 8 pages excluding translation.
Chinese Second Office Action for Application No. 201480014965.4, dated Oct. 23, 2017, 3 pages.
Chinese Second Office Action for Application No. 201480014971.X, dated Aug. 16, 2017, 3 pages excluding translation.
Chinese Second Office Action for Application No. 201480015065.1, dated Sep. 8, 2017, 3 pages excluding translation.
Chinese Third Office Action for Application No. 2014800143520, dated Sep. 26, 2017, 4 pages excluding translation.
European Office Action for Application No. 14/708451.1, dated Nov. 30, 2016, 3 pages.
European Office Action for Application No. 14158885.5, dated Dec. 16, 2015, 5 pages.
European Office Action for Application No. 14158899.6, dated Feb. 12, 2020, 5 pages.
European Office Action for Application No. 14158899.6, dated Sep. 13, 2017, 4 pages.
European Office Action for Application No. 14708450.3, dated Oct. 25, 2017, 4 pages.
European Office Action for Application No. 14709077.3, dated Sep. 19, 2017, 6 pages.
Extended European Search Report and Written Opinion for Application No. 17158061.6, dated Jun. 20, 2017, 7 pages.
Extended European Search Report for Application No. 14778965.5, dated May 9, 2017, 13 pages.
Extended European Search Report for Application No. 18155594.7, dated May 15, 2018, 8 pages.
Extended European Search Report for Application No. 20153180.3, dated Feb. 19, 2020, 7 pages.
Extended European Search Report for Application No. 20191909.9, dated Nov. 17, 2020, 7 pages.
Extended European Search Report for Application No. 22152244.4, dated May 12, 2022, 7 pages.

(56) References Cited

OTHER PUBLICATIONS

Extended European Search Report in European Application No. 14158882.2 dated Jul. 7, 2014, 7 pages.
Extended European Search Report in European Application No. 14158885.5 dated May 12, 2014, 11 pages.
Extended European Search Report in European Application No. 14158891.3 dated Jul. 8, 2014, 6 pages.
Extended European Search Report in European Application No. 14158894.7 dated May 12, 2014, 8 pages.
Extended European Search Report in European Application No. 14158899.6 dated Jul. 8, 2014, 6 pages.
India Office Action for Application No. 202038001860, dated Feb. 15, 2021, 7 pages.
India Office Action for Application No. 202038022435, dated Oct. 27, 2021, 9 pages.
India Office Action for Application No. 2764/KOLNP/2015, dated Feb. 5, 2020, 8 pages.
India Office Action for Application No. 2780/KOLNP/2015, dated Sep. 17, 2019, 8 pages.
India Office Action for Application No. 3149/KOLNP/2015, dated Jul. 29, 2019, 5 pages.
India Office Action for Application No. 3248/KOLNP/2015, dated Jul. 30, 2019, 5 pages.
India Office Action for Application No. 3370/KOLNP/2015, dated Sep. 26, 2019, 8 pages.
Indian Office Action for Application No. 2748/KOLNP/2015, dated Sep. 4, 2020, 6 pages.
International Search Report and Written Opinion in PCT Application No. PCT/US2014/017480 mailed May 13, 2014, 13 pages.
International Search Report and Written Opinion in PCT Application No. PCT/US2014/017486 mailed May 13, 2014, 14 pages.
International Search Report and Written Opinion in PCT Application No. PCT/US2014/017824 mailed May 9, 2014, 21 pages.
International Search Report and Written Opinion in PCT Application No. PCT/US2014/017826 mailed May 8, 2014, 10 pages.
International Search Report and Written Opinion in PCT Application No. PCT/US2014/017828 mailed May 2, 2014, 10 pages.
International Search Report and Written Opinion in PCT Application No. PCT/US2014/023694 mailed Jun. 26, 2014, 11 pages.
International Written Opinion of the International Preliminary Examining Authority for International Application No. PCT/US2014/017824, dated Mar. 23, 2015, 6 pages.
International Written Opinion of the International Preliminary Examining Authority for International Application No. PCT/US2014/017828, dated Mar. 20, 2015, 6 pages.
Japanese Office Action for Application No. 2016-500315, dated Mar. 9, 2018, 3 pages excluding English translation.
Japanese Office Action for Application No. 2016-500315, dated Nov. 24, 2017, 2 pages excluding translation.
Japanese Office Action for Application No. 2016-500317, dated Oct. 25, 2017, 4 pages excluding translation.
Japanese Office Action for Application No. 2016-500341, dated Mar. 9, 2018, 3 pages excluding English translation.
Japanese Office Action for Application No. 2016-500341, dated Nov. 24, 2017, 2 pages excluding translation.
Japanese Office Action for Application No. 2016-500342, dated Nov. 28, 2017, 4 pages excluding English translation.
Japanese Office Action for Application No. 2016-500343, dated Dec. 21, 2017, 3 pages excluding translation.
Japanese Office Action for Application No. 2016-500343, dated Jul. 1, 2018, 2 pages.
Japanese Office Action for Application No. 2016-501317, dated Jan. 16, 2018, 5 pages excluding English translation.
Japanese Office Action for Application No. 2018-145746, dated Jul. 2, 2019, 8 pages.
Japanese Office Action for Application No. 2018-223368, dated Oct. 29, 2019, 7 pages.
Japanese Office Action for Application No. 2019-088804, dated Jan. 22, 2021, 4 pages including translation.
Japanese Office Action for Application No. 2019-088804, dated May 26, 2020, 8 pages.
Japanese Office Action for Application No. 2019-207187, dated Sep. 29, 2020, 8 pages.
Japanese Office Action for Application No. 2020130129, dated Jun. 1, 2021, 6 pages including translation.
Japanese Office Action for Application No. 2021-022518, dated Oct. 28, 2021, 11 pages including translation.
Japanese Office Action for Application No. 2021-182971, dated Aug. 30, 2022, 4 pages including translation.
Japanese Office Action for Application No. 2021-182971, dated Jan. 5, 2023, 4 pages including translation.
Japanese Office Action for Application No. 2021-182971, dated Jun. 2, 2023, 6 pages including translation.
Japanese Office Action for Application No. 2022-029206, dated Feb. 16, 2023, 4 pages.
Japanese Office Action for Application No. 2022029206, dated Sep. 12, 2023, 4 pages including translation.
Partial Supplementary European Search Report for Application No. 14778965.5, dated Dec. 16, 2016, 7 pages excluding translation.
Canadian Office Action for Application No. 3,205,802, dated Nov. 20, 2024, 3 pages.
Japanese Office Action for Application No. 2023-176606, dated Sep. 27, 2024, 4 pages including translation.
Chinese Invalidation Request for Application No. 201810058864.7 (Chinese Patent No. ZL 2018100588647 (CN108295374B)), dated Apr. 18, 2025, 36 pages including machine translation.
Chinese Notice of Transfer of Documents for Application No. 201810058864.7 (Chinese Patent No. ZL 2018100588647 (CN108295374B)), dated Jun. 16, 2025, 80 pages including machine translation.
Chinese Notice of Acceptance of Request for Invalidation for Application No. 201810058864.7 (Chinese Patent No. ZL 2018100588647 (CN108295374B)), dated Apr. 23, 2025, 8 pages including machine translation.
Canadian Office Action for Application No. 3,205,802, dated Jul. 7, 2025, 4 pages.
Japanese Office Action for Application No. 2025-035217, dated Dec. 3, 2025, 4 pages including translation.
Chinese Second Re-Examination Notice for Patent Application No. 201910444553.9, dated Nov. 11, 2025, 10 pages including English summary.
European Office Action for Application No. 23158100.0, dated Feb. 20, 2026, 7 pages.
Chinese Re-examination Decision for Application No. 201910444553.9, dated May 19, 2026, 12 pages including translation.

* cited by examiner 231
272
301
250
282A
282B
282C
260
272

232
272
250
285A
285B
285C
260
272

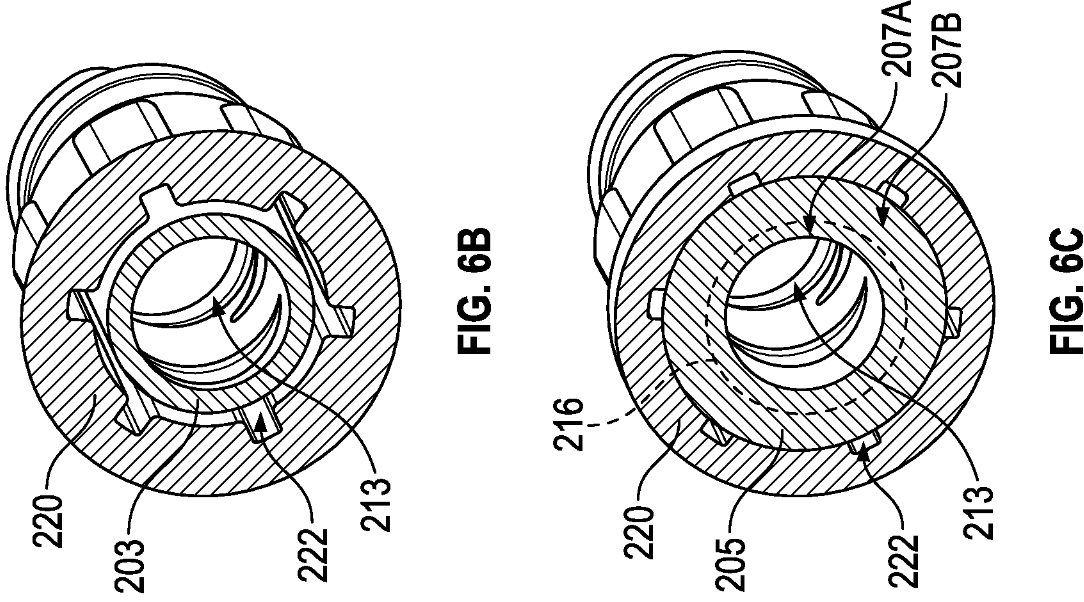
FIG. 6B
FIG. 6C
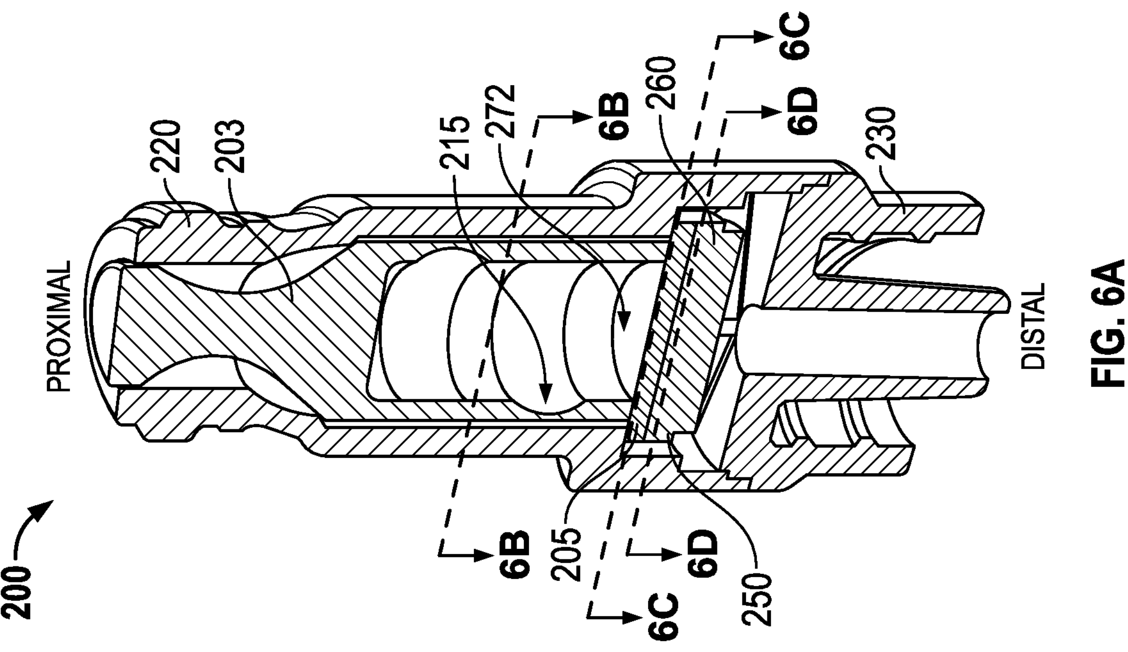
FIG. 6A

NEEDLELESS CONNECTOR WITH SUPPORT MEMBER

CROSS-REFERENCE TO RELATED APPLICATIONS

The present application is a continuation of U.S. application Ser. No. 17/323,835, filed May 18, 2021, which is a continuation of U.S. application Ser. No. 14/745,199, filed Jun. 19, 2015, now U.S. Pat. No. 11,033,726, entitled, "NEEDLELESS CONNECTOR WITH SUPPORT MEMBER," which is a continuation of U.S. application Ser. No. 13/829,187, filed Mar. 14, 2013, now U.S. Pat. No. 9,089,682, entitled, "NEEDLELESS CONNECTOR WITH SUPPORT MEMBER," the disclosure of each of which are incorporated herein by reference in their entireties.

BACKGROUND

The present disclosure generally relates to connectors, and, in particular, to needleless connectors.

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, an IV bag. Certain needleless connectors may be used in an IV set and may have a self-sealing port to prevent leakage of fluid when a mating medical implement is decoupled from such a needleless connector. Additionally, a needleless connector may include a mechanical valve, for example, a collapsible valve comprising a flexible material for providing the self-sealing port and controlling the flow of fluid within the IV set.

When a needleless connector is used in an IV set but not being accessed (i.e., a mating medical implement is not coupled to the self-sealing port), the needleless connector may be subjected to back pressure from the flow of fluid within the IV set. For example, back pressure can be caused by a patient's blood pressure, by an injection made at a different connector in the IV set, or by a pump utilized in the IV set. Back pressure applied to some needleless connectors may cause the seal of the self-sealing port to be breached. If the seal of a non-accessed needleless connector becomes breached due to back pressure, then some medical fluid from the IV set may undesirably accumulate in the neck area of the self-sealing port or be expelled from the system.

SUMMARY

The disclosed subject matter relates to connectors having support members for collapsible valves. In certain embodiments, a needleless connector is disclosed that comprises a body; a valve element at least partially disposed within the body, the valve element comprising a cylindrical portion having an outwardly extending flange at a distal end, the flange having a bottom surface with an outer area and an inner area; and a base comprising a rim having a top surface that is in contact with at least a portion of the outer area of the flange of the valve element, the rim defining a recess with a bottom surface distally separated from the top surface of the rim, and at least one support member extending from the rim into the recess so as to contact the inner portion of the bottom surface of the flange.

In certain embodiments, a needleless connector is disclosed that comprises a housing comprising proximal and distal ends, a body having a female fitting with a port at the proximal end, a base having a male fitting at the distal end, and an internal cavity; a valve element disposed within the internal cavity and comprising a proximal portion having a smiley cut, a cylindrical portion coupled to a distal end of the proximal portion, and an outwardly extending flange coupled to the distal end of the cylindrical portion, the flange having a bottom surface with an outer area and an inner area; and a base comprising a rim having a top surface that is in contact with at least a portion of the outer area of the bottom surface of the flange of the valve element, the rim defining a recess in the base, the recess having a bottom surface distally separated from the top surface of the rim, and a plurality of protrusions each extending from the rim into the recess so as to contact the inner portion of the bottom surface of the flange, wherein the proximal portion of the valve element blocks the port when the female fitting of the needleless connector is not mated with a compatible male connector.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 6A is a cut-away perspective view of the assembled needleless connector of FIG. 2, in accordance with various aspects of the present disclosure.

FIGS. 6B-6D are cut-away perspective views of the complete connector at locations shown in FIG. 6A, in accordance with various aspects of the present disclosure.

DETAILED DESCRIPTION

Figure 1B:
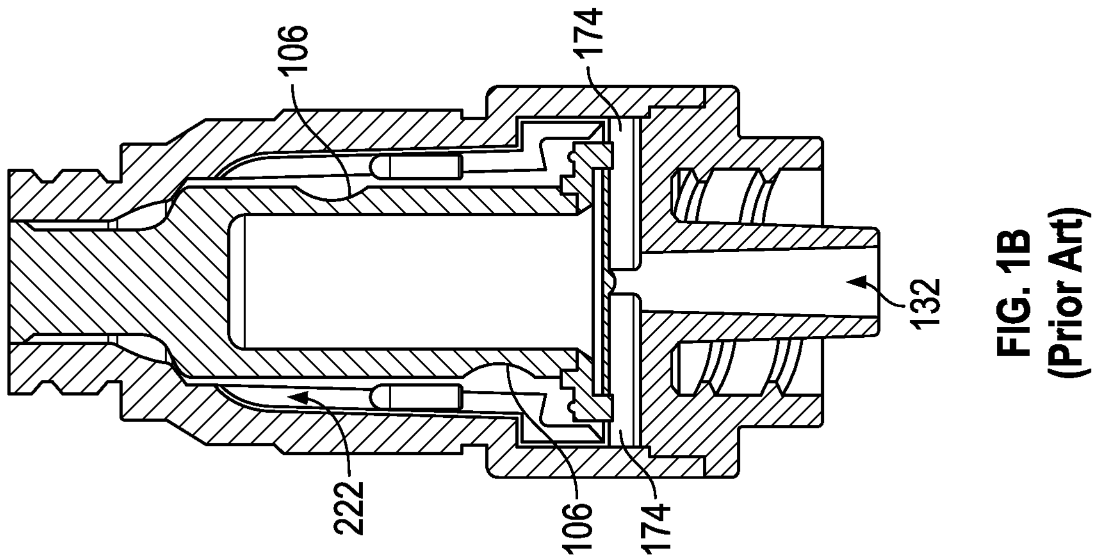
FIGS. 1A and 1B are cross-sections of a conventional needleless connector.

The disclosed self-sealing, needleless connector incorporates a flexible, collapsible valve disposed within a body of the connector. A bottom surface of the collapsible valve is in contact with support members of a base that support the collapsible valve when back pressure is applied to the needleless connector in order to prevent deformation of the collapsible valve toward the base. By preventing deformation of the collapsible valve toward the base, the back pressure deforms the collapsible valve in a manner that further improves the seal of the needleless connector when in a non-accessed state.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to the administration of medical fluid to a patient by a medical practitioner using the disclosed needleless connector, it is to be understood that this description is only an example of usage and does not limit the scope of the claims. Various aspects of the disclosed needleless connectors may be used in any application where it is desirable to prevent a valve from breaching a primary seal when in the connector is in a non-accessed state.

The disclosed needleless connector overcomes several challenges discovered with respect to certain conventional connectors. One challenge with certain conventional needleless self-sealing connectors is that a primary seal may be breached when the self-sealing connectors are subjected to back pressure from the flow of fluid within an IV set. Because such a breach of the primary seal may result in the malfunction of the connector and failure in the administration of the medical fluid, such a breach is undesirable.

Therefore, in accordance with the present disclosure, it is advantageous to provide a needleless connector as described herein that eliminates or substantially reduces potential back pressure-related problems within the needleless connector during use without unduly limiting an air channel of the needleless connector. The disclosed needleless connector provides a support member on a base that substantially prevents the flexible valve from extending into a recess of the base.

Figure 1A:
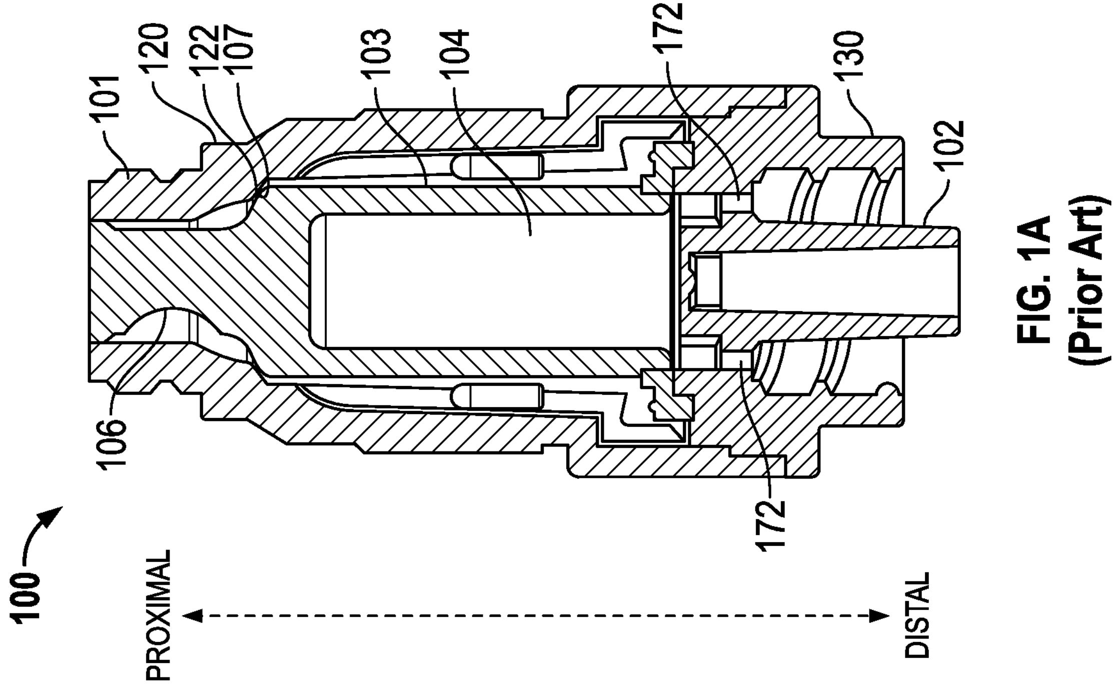

FIGS. 1A and 1B are cross-sections of a conventional needleless connector 100. Connector 100 includes a housing 120, which has female luer fitting 101 at the proximal end, a base 130, which has male luer fitting 102 at the distal end, and a valve element 103. The valve element 103 sits inside housing portion 120 and on top of the base 130. The proximal portion of valve element 103 has a "smiley cut" 106. Air channels 172 pass from the internal cavity 104 of the valve element 103 through the base 130 into the open space around the male Luer fitting 102. The valve element 103 has a shoulder 107 that continuously contacts a ridge 122 within the interior of the housing 120, when the needleless connector 100 is not being accessed (i.e., a mating medical implement is not coupled to the self-sealing port) to form a primary seal that prohibits fluid of the fluid flow channels 174 from exiting the needleless connector 100 through the female luer fitting 101.

The cross-section of FIG. 1B is taken perpendicular to the cross-section of FIG. 1A. In this view, the two dimples 106 formed in an external surface of the valve element 103 are visible. Fluid flow channels 174 pass from a cavity 22 within the housing 120 through the base 130 to a flow passage 132 within the male Luer fitting 102.

Figure 1D:
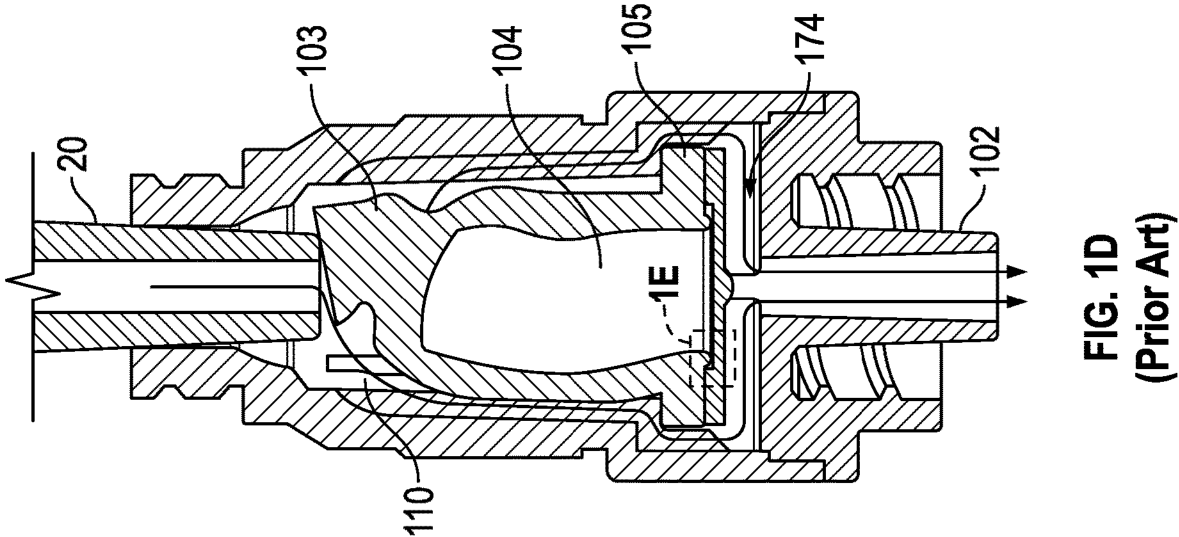
FIG. 1D is a cross-section of the conventional connector of FIG. 1A when mated with compatible male connector.
Figure 1C:
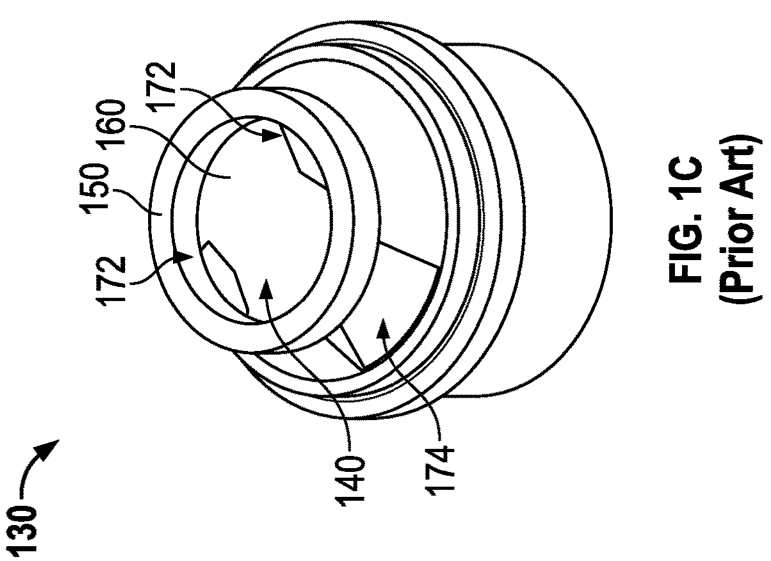
FIG. 1C is a perspective view of the base of the conventional connector of FIG. 1A.

FIG. 1C is a perspective view of the base 130 of the conventional connector 100 of FIG. 1A. The base 130 has a rim 150 surrounding a recess 140 with a bottom surface 160. The valve base 105 of the valve element 103 (not shown in FIG. 1C) fits over the rim 150. The entrances to the air channels 172 are visible within the cavity 140. The entrance to one of the fluid flow channels 174 is visible on the side of the base 130.

FIG. 1D is a cross-section of the conventional connector 100 of FIG. 1A when mated with compatible male connector 20. In operation, when the female fitting 101 of the connector 100 is accessed by a male fitting 20, the valve element 103 is sufficiently elastic so that it can bend out of the way to allow fluid flow and then return to its original shape after the male fitting 20 is disconnected. The collapsible valve element 103 is shown in a collapsed position after insertion of the male connector 20 into female fitting 101. Fluid can flow from the male connector 20 around the collapsed valve element 103 is into channels including the fluid flow channels 174 of the base 130 and into the male luer fitting 102 for exiting the connector 100. The valve base 105 of the valve element 103 deformed under the pressure of the male connector 20, with the deformation being described in greater detail with respect to FIG. 1E.

Connector 100 is a positive displacement device. When a new connection is made at the female fitting 101, the internal cavity 104 is reduced and the connector 100 draws fluid in either through the female fitting 101 or the male fitting 102 of the base 130 via the fluid channel 222. When a disconnection is made at the female luer fitting 101, the connector 100 expels fluid from the fluid channel 222, effectively flushing the connector 100 and, if one of the lines attached to fittings 101 or 102 are connected to a patient, avoids drawing blood into the line.

Figure 1F:
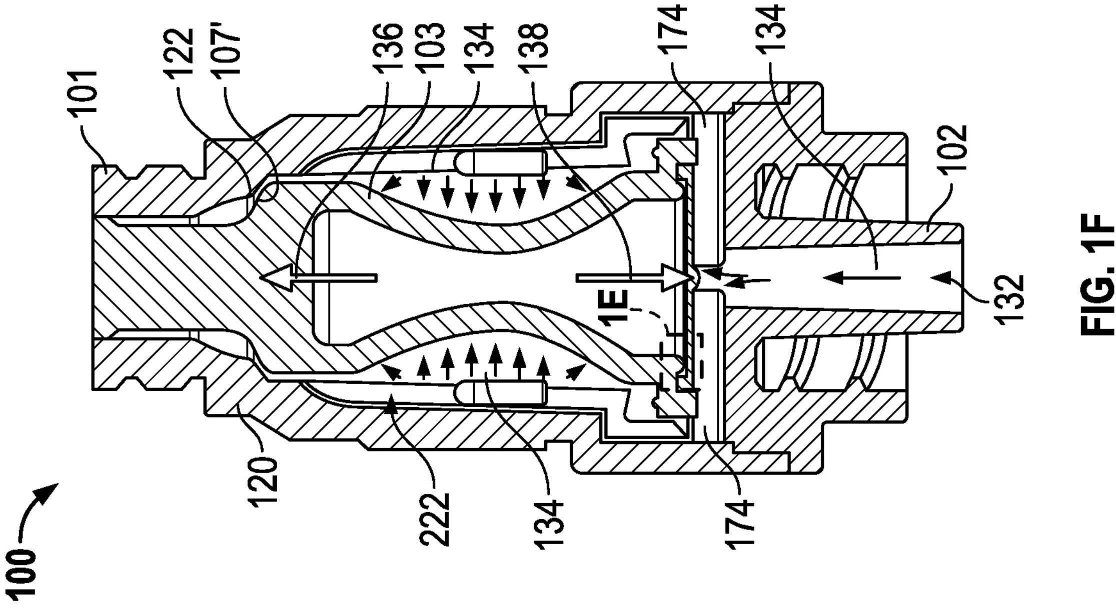
FIG. 1F is a cross-section of the conventional connector of FIG. 1A when the conventional connector is in a fluidly connected, but non-accessed, state.

FIG. 1F is a cross-section of the conventional connector 100 of FIG. 1A when the male connector 20 (shown in FIG. 1D) has been removed and back pressure 134 is applied to the valve element 103 from the fluid channel 222 fluidly connected to a line (not shown) attached to the male fitting 102 of the base 130. When back pressure 134 is applied within the interior of the housing 120, the generally cylindrical shape of the valve element 103 is deformed to a generally oval-tubular shape. A proximal force 136 and a distal force 138 result from the deformation of the valve element 103 due to its flexible, collapsible properties. If the distal force 138 substantially counteracts the proximal force 136, then the shoulder 107' may cease to contact the ridge 122 within the interior of the housing 120, thereby causing a breach of the primary seal of the needleless connector 100. As similarly discussed with respect to the force applied by the male connector 20 in FIG. 1C, the valve base 105 of the valve element 103 is deformed under the pressure of the distal force 138 caused by back pressure 134 of the fluid entering the flow passage 132, with the deformation being described in greater detail with respect to FIG. 1E.

Figure 1E:
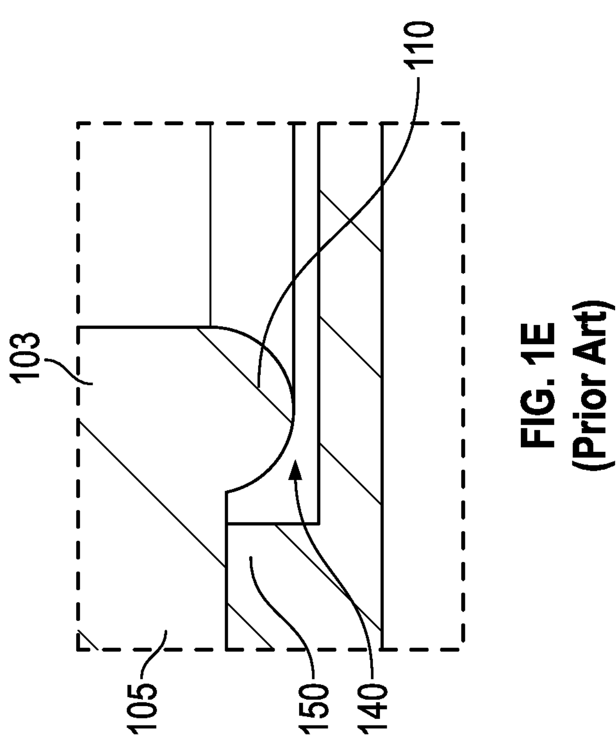
FIG. 1E is an enlarged view of a portion of FIG. 1D.

FIG. 1E is an enlarged view of a portion of FIG. 1D and FIG. 1F. The compressive load from the male fitting 20 (see FIG. 1D) or the distal force 138 caused by back pressure 134 (see FIG. 1F) is transferred by the wall of the valve element 103 to the valve base 105 and then into the rim 150. Due to the flexible nature of the valve element 103, however, the interior corner 110 of the valve base 105 may deform and protrude into the cavity 140 as seen in FIG. 1E.

An example of a needleless connector that eliminates or substantially reduces undesirable deformation of the valve element during use is now described.

Figure 2:
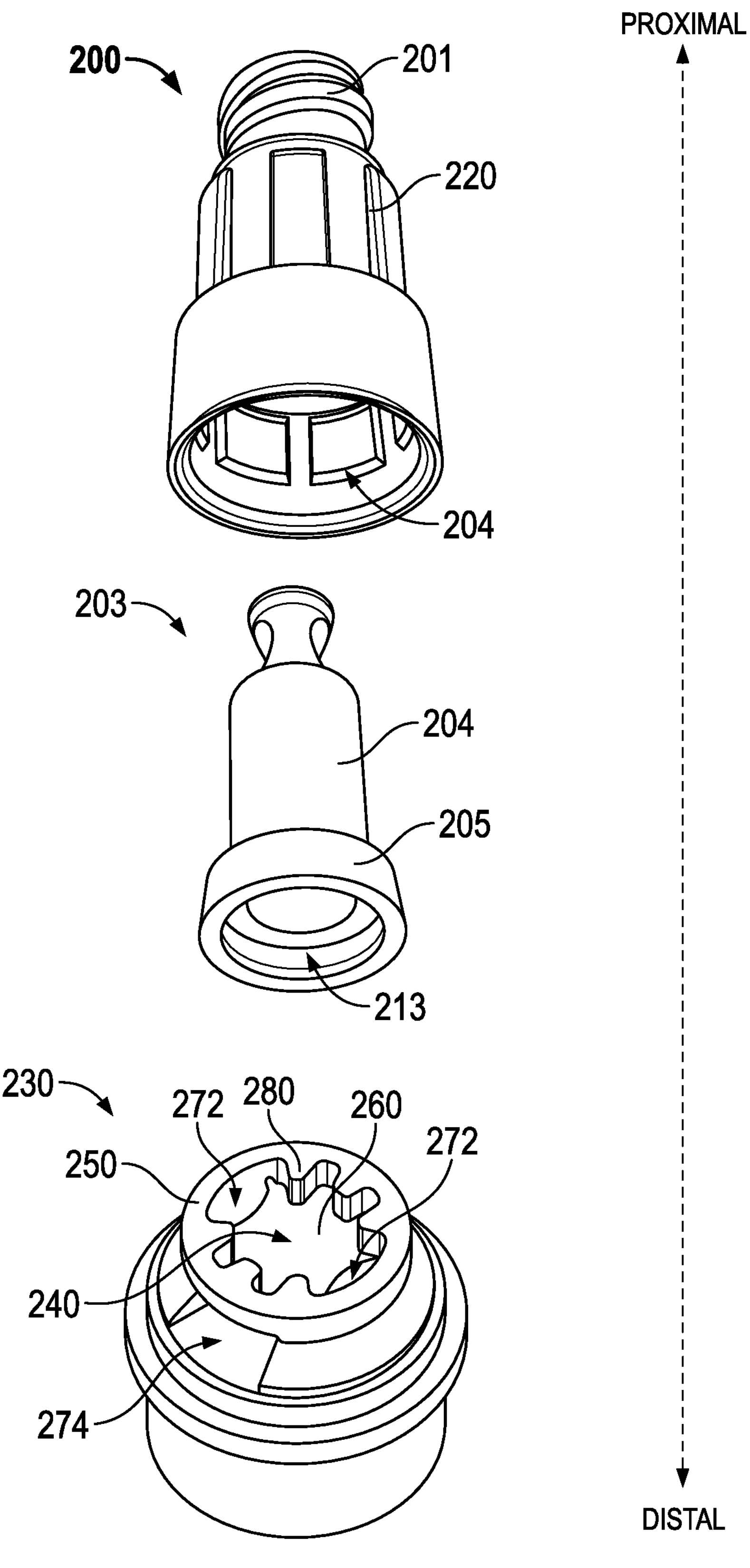
FIG. 2 is an exploded view of an exemplary needleless connector, in accordance with various aspects of the present disclosure.

FIG. 2 is an exploded view of an exemplary needleless connector 200, in accordance with various aspects of the present disclosure. The connector 200 includes a body 220 defining an internal cavity 204 and having a female fitting 201, a flexible valve element 203 having a cylindrical portion with a flange 205 extending outward at a distal end of the cylindrical portion 204 and an interior volume 213, and a base 230. The base 230 has a rim 250 that defines a recess 240 with two air passages 272 passing from a recess 240 through the body 230 to the ambient environment around the male fitting (not visible in FIG. 2), and one or more support members 280 that extend from the rim 150 laterally into the recess 240. When assembled, a top surface of the rim 250 is in contact with the valve base or flange 105. The recess 240 has a bottom surface 260 that is distally separated from the top surface of the rim 250. Two passages 274 (only one visible in FIG. 2) pass through the base 230 and are configured similar to passages 174 in FIGS. 1B and 1C.

In certain embodiments, the base 230 comprises a polycarbonate material. However, the base 230 as well as the body 220 of the connector 100 may comprise one or more materials including, but not limited to, polyester, polyethylene, and/or other thermoplastics. Additionally, one or both of the base 230 and the body 220 may be clear or translucent, thereby enabling partial visibility of fluid within the connector 200. In certain embodiments, the flexible valve element 203 comprises a silicone.

In certain embodiments, the needleless connector 200 may have certain similar characteristics and functionality similar to that of the conventional connector 100. For example, in certain embodiments, the needleless connector 200 includes certain aspects that are different from the connector 100 such as a smaller overall length, smaller port diameter, smaller fluid path channels, smaller overall diameter, different valve operation, different materials composition, etc. For example, in certain embodiments, base section 230 is smaller than base 130. In this regard, certain embodiments derive a benefit from the base section having a support member.

As illustrated, the recess 240 of the base 230 is aligned to interface with the interior volume 213 of the flexible valve element 203 upon assembly. Embodiments of the support members 280 provide a mechanism for eliminating or substantially reducing intrusion of the flexible valve element 203 into the recess 240. Various examples of the configuration of support members 280 are discussed with respect to FIGS. 3-5. When assembled, the flange 205 of the flexible valve element 203 is captured between the body 220 and base 230, as is discussed in greater detail with respect to FIG. 6.

Figures 3, 4, 5:
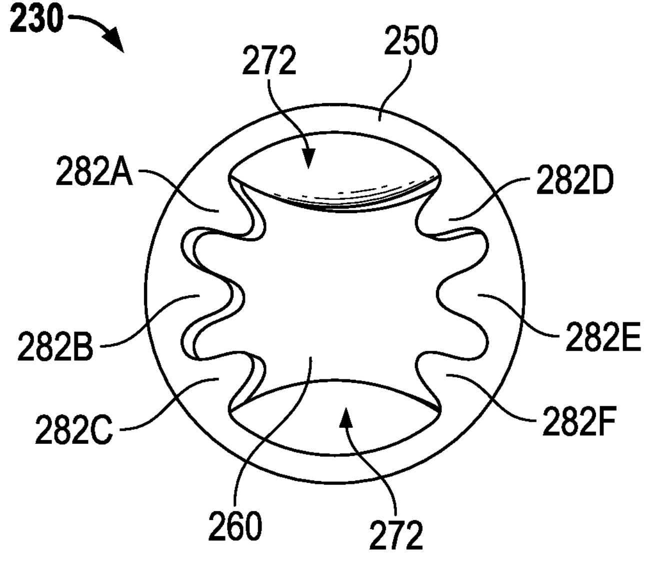
FIG. 3 is a top view of the base of FIG. 2, in accordance with various aspects of the present disclosure.
FIGS. 4 and 5 are top views of other embodiments of the base, in accordance with various aspects of the present disclosure.

FIG. 3 is a top view of the base 230 of FIG. 2, in accordance with various aspects of the present disclosure. In this example embodiment, six protrusions 282A-282F are disposed along portions of the rim 250 and longitudinally extend into recess 240. In certain embodiments, there may be more or fewer protrusions 280. In certain embodiments, the protrusions 282A-282F have rounded tips as shown in FIG. 3. In certain embodiments, the protrusions 282A-282F may have sharp corners or straight edges. One or more of the protrusions 282A-282F may be disposed over the bottom surface 260. In the example shown in FIG. 3, all six of the protrusions 282A-282F are fully over the bottom surface 260, i.e. no portion of the protrusions 282A-282F overhang either of the flow passages 272. In this regard, the protrusions 280A-280F are arranged such that the cross-sectional area of the air passage 272 is not reduced or obstructed while providing support for the flange 205 of the valve member 203. Obstructing or reducing the cross-sectional area of the air passage 272 could decrease the performance of the valve member 203 in certain embodiments, for example, when air is required to rapidly escape or enter the interior volume 213 of the valve member 203 while collapsing or expanding, respectively. In some embodiments, one or more protrusions 280 may extend partially or completely over one of the air passages 272. The support of the flange 205 that is provided by the protrusions 280A-280F is discussed in greater detail with respect to FIG. 6D.

FIGS. 4 and 5 are top views of other embodiments 231, 232 of the base, in accordance with various aspects of the present disclosure. FIG. 4 illustrates another example of a base 231 having protrusions 282A-282C disposed over a portion of rim 250 on one side of a center axis 301 and no protrusions on the other side of axis 301. Provision of protrusions 282A-282C on a single side may provide, for example, improved control of the collapse of the flexible valve element 203.

FIG. 5 illustrates another example of a base 232. According to certain embodiments, the base 232 comprises one or more support ribs 285A-285C. In this example, each of the ribs 285A-285C extends across the recess 240 from a first portion of the rim 250 to a second portion of the rim 250. In some embodiments, the ribs 285A-285C are the full height of rim 250 and continuous for the entire length of the respective ribs 285A-285C. In other embodiments, one or more of the ribs 285A-285C may have open segments proximal the bottom surface 260 to facility an air pathway across the bottom surface 260 between the two apertures 272. In certain embodiments, each rib 285A-285C may be integral with the wall 250 and/or bottom 260 of the base 230.

In some embodiments, the support members 280, for example the protrusions 282 of FIG. 3 and/or the ribs 285 of FIG. 5, may extend between 0.01 and 0.15 inches above the rim 250. In certain embodiments, the support members 280 may extend 0.05 inches above the rim 250. In certain embodiments, the support members 280 may extend the same longitudinal length. In other embodiments, the support members 280 may have different longitudinal lengths. In certain embodiments, the support members 280 may have various portions that are recessed below, flush with, or raised above the top surface of the rim 250.

Figure 6D:
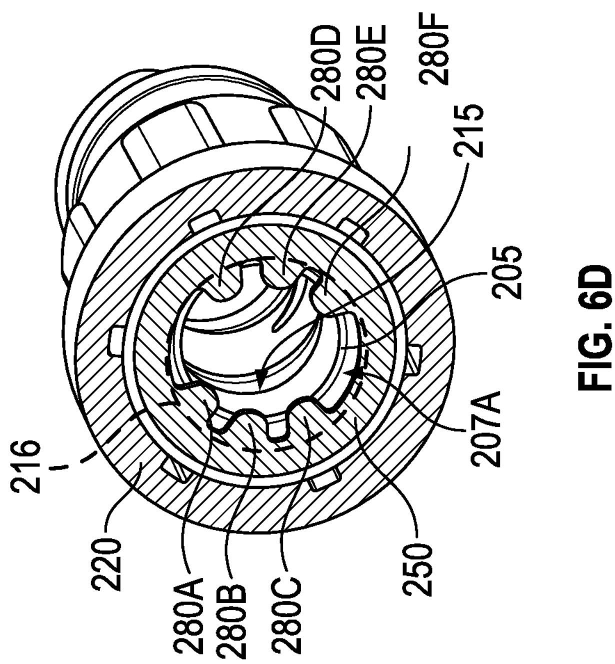

FIG. 6A is a cut-away perspective view of the assembled needleless connector 200 of FIG. 2, in accordance with various aspects of the present disclosure. The flange 205 has engaged the rim 250 of base 230, and then the body 220 placed over the flexible valve element 203 and sealingly coupled to the body 230, thereby capturing a portion of the flange 205 between the body 220 and base 230. The various sections B-B, C-C, and D-D are shown in FIGS. 6B-6D, respectively. The top opening to one of the air channels 272 is visible adjacent to the bottom surface 260. This embodiment of valve element 203 has internal dimples 215 that extend over a portion of a circumference of the surface of the internal volume 213.

FIGS. 6B-6D are cut-away perspective views of the complete connector 200 at locations shown in FIG. 6A, in accordance with various aspects of the present disclosure. FIG. 6B is taken above the flange 205 and shows the cylindrical portion of the valve element 203 disposed within the body 220. The interior volume 213 is visible within the valve element 203 while fluid channels 222 are visible as formed in the interior wall of body 220 and external to the valve element 203.

FIG. 6C depicts a cross-section taken at the bottom surface of the flange 205. The outer diameter of the flange 205 has extended radially outward while maintaining an inner diameter matching the interior volume 213. The lower portions of fluid channels 222 are visible and provide the fluid flow path around the flange 205. The dash-line circle 216 indicates a projection of the outer surface of the cylindrical portion 204 onto the cross-sectional surface. In certain embodiments, the circle 216 divides the bottom surface of the flange 205 into an inner area 207A and an outer area 207B.

FIG. 6D depicts a cross-section taken through the protrusions 280A-280F just below the bottom surface of the flange 205. It can be seen how the protrusions 280A-280F extend inward over the inner area 207A and past the inner diameter of the flange 205, thereby providing complete support to the flange 205 and preventing the deformation seen in the conventional connector 100, for example as shown in FIG. 1E. In certain embodiments, the protrusions 280A-280F may be aligned, or oriented in a defined relationship, with respect to the dimples 215 of the valve element 203. In certain embodiments, one or more of the protrusions 280A-280F may not extend past the inner diameter of the flange 205.

Figure 7:
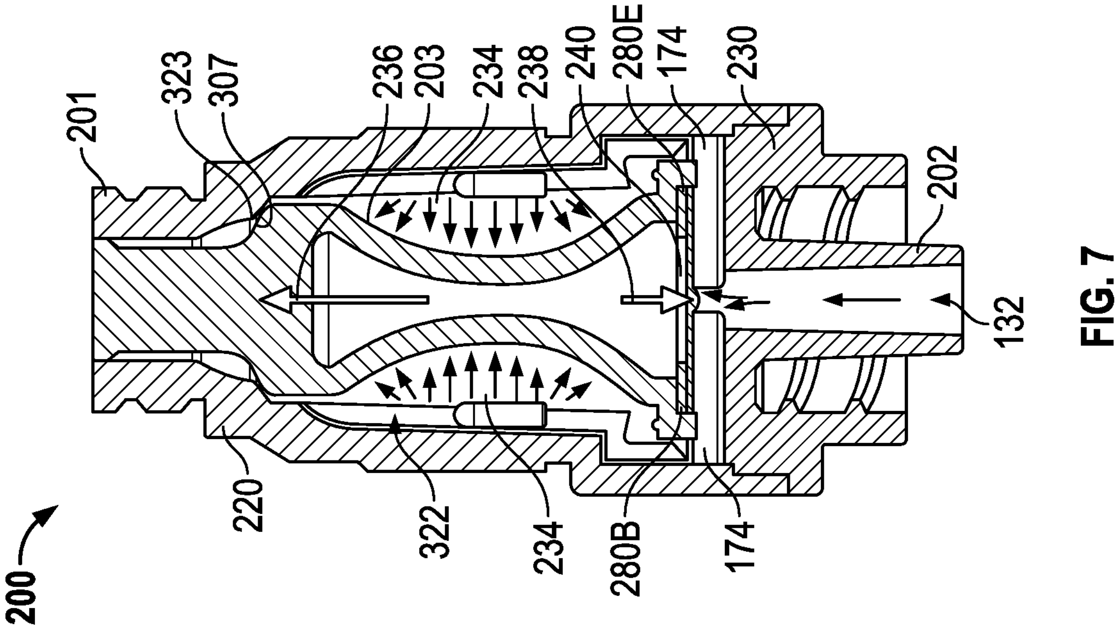
FIG. 7 is a cross-section of an exemplary needleless connector of FIG. 2 when the exemplary needleless connector is in a fluidly connected, but non-accessed, state, in accordance with various aspects of the present disclosure.

Referring to FIG. 7, an exemplary needleless connector 200 is shown when the needleless connector 200 is in a fluidly connected, but non-accessed state. As illustrated, the needleless connector 200 is being subjected to back pressure 234 applied to the valve element 203 from the fluid channel 322 fluidly connected to a line (not shown) attached to the male fitting 202 of the base 230. The base 230 has protrusions 280A-280F that provide support the valve element 203, particularly the flange 205, when back pressure 234 is applied to the valve element 203 within the body 220. Thus, the protrusions 280A-280F of the base 230 eliminate or substantially prevent deformation of the flange 205 into the recess 240 of the base 230. Therefore, in contrast with FIG. 1F, a proximal force 236 caused by back pressure 234 will be increased and a distal force 238 will be eliminated or substantially reduced. Accordingly, movement of the valve element 203 will occur in the proximal direction toward the female fitting 201, thereby further improving the primary seal of the needleless connector 200 between a shoulder 307 of the valve element 203 and an interior ridge 323 of the body 220 when being subjected to back pressure 234 in the fluidly connected, but non-accessed state.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A needleless connector comprising:

a body section comprising a first port and an inner surface having fluid channels and forming an internal cavity;

a base section comprising a rim at a top of the base section, a second port at a bottom of the base section, and an air passage through the base section to an outer surface of the base section, the rim extending laterally outward away from a central longitudinal axis, the rim defining a recess with a bottom surface distally separated from a top surface of the rim, and the rim defining support members extending from the rim into the recess; and a compressible valve comprising a valve wall and a flange protruding radially outward from an outer surface of the valve wall, the flange comprising an outer surface and an inner surface, wherein, when the compressible valve is coupled with the base section, the flange is compressed between the body section and the rim of the base section, the fluid channels form a fluid flow path around the flange and between the outer surface of the valve wall and the inner surface of the body, and the air passage forms an air flow path between an internal cavity of the compressible valve to the outer surface of the base section.

2. The needleless connector of claim 1, wherein the valve wall comprises a first dimple and a second dimple formed in an inner surface of the compressible valve.

3. The needleless connector of claim 1, wherein the support members extend in a direction toward the central longitudinal axis.

4. The needleless connector of claim 1, wherein, when a back pressure is applied to the compressible valve from the fluid channels, the support members resist movement of the flange into the recess.

5. The needleless connector of claim 1, wherein an air passage extends through the recess, and wherein the support members do not extend over the air passage.

6. The needleless connector of claim 1, wherein the support members comprise a height aligned with the rim of the base section.

7. The needleless connector of claim 1, wherein a height of the support members extends between 0.02 cm (0.01 inch) and 0.38 cm (0.15 inch) above the rim.

8. The needleless connector of claim 1, wherein a height of the support members extends 0.13 cm (0.05 inch) above the rim.

9. The needleless connector of claim 1, wherein the support members comprise a longitudinal length from the rim into the recess, and each of the support members have the same longitudinal length.

10. The needleless connector of claim 1, wherein the base section comprises a flow channel and a flow passage, the flow channel extending through an outer surface of the base section to the flow passage within the second port.

11. The needleless connector of claim 1, wherein support members are disposed on one side of a center axis of the base section.

12. The needleless connector of claim 1, wherein support members extend across the recess of the base section, from a first portion of the rim to a second portion of the rim.

13. The needleless connector of claim 12, wherein the support members comprise an opening proximal to a bottom surface defined by the recess of the base section and between two air passages through the base section.

14. The needleless connector of claim 12, wherein the support members are formed by any of the rim and a bottom surface defined by the recess of the base section.

15. A needleless connector comprising:

a body section comprising an inner surface forming an internal cavity, a proximal end of the body section defining a female luer fitting, wherein the inner surface forms fluid channels;

a base section comprising a distal end of the base section defining a male luer fitting, a proximal end of the base section defining a rim that extends in a first direction that is transverse relative to a central longitudinal axis of the base section, the rim defining a recess with a bottom surface distally separated from a top surface of the rim, and the rim defining support ribs integral with the rim and extending from the rim into the recess in a second direction that is different than the first direction, and an air passage through the base section to an outer surface of the base section, wherein the support ribs extend across the recess, from a first portion of the rim to a second portion of the rim; and a compressible valve comprising a valve wall and a flange protruding radially from the valve wall, the flange comprising an outer surface and an inner surface, wherein, when the compressible valve is coupled with the body section and the base section, the flange is compressed between the body section and the rim of the base section, the fluid channels form a fluid flow path around the flange and between the outer surface of the valve wall and the inner surface of the body, and the air passage forms an air flow path between an internal cavity of the compressible valve to the outer surface of the base section.

16. The needleless connector of claim 15, wherein the base section comprises a flow channel and a flow passage, the flow channel extending through an outer surface of the base section to the flow passage within the male luer.

* * * * *